United States Patent [19]

Wei

[11] Patent Number: 5,306,710
[45] Date of Patent: Apr. 26, 1994

[54] METHOD FOR TREATING ENDOTOXIN SHOCK WITH CRF

[75] Inventor: Edward T. Wei, Berkeley, Calif.

[73] Assignee: Regents of the University of California, Oakland, Calif.

[21] Appl. No.: 876,487

[22] Filed: Apr. 30, 1992

Related U.S. Application Data

[62] Division of Ser. No. 386,885, Jul. 28, 1989, Pat. No. 5,137,871.

[51] Int. Cl.$^5$ .............................. A61K 37/40
[52] U.S. Cl. ......................... 514/12; 530/306
[58] Field of Search ............... 514/12; 530/306

[56] References Cited

U.S. PATENT DOCUMENTS

| | | | |
|---|---|---|---|
| 3,980,778 | 9/1976 | Ayer et al. | 514/12 |
| 4,404,198 | 9/1983 | Kelley | 514/12 |
| 4,415,558 | 11/1983 | Vale, Jr. et al. | 514/12 |
| 4,489,163 | 12/1984 | Rivier et al. | 514/12 |
| 4,517,181 | 5/1985 | Ling et al. | 514/12 |
| 4,528,189 | 7/1985 | Lederis et al. | 514/12 |
| 4,533,654 | 8/1985 | Lederis et al. | 514/12 |
| 4,579,844 | 4/1986 | Rovee et al. | 514/12 |
| 4,594,329 | 6/1986 | Vale, Jr. et al. | 514/12 |
| 4,605,642 | 8/1986 | Rivier et al. | 514/12 |
| 4,801,612 | 1/1989 | Wei et al. | 514/12 |
| 5,137,871 | 8/1992 | Wei | 514/12 |

OTHER PUBLICATIONS

Chan et al., "Phospholipid Degradation and Edema Development in Cold-Injured Rat Brain", *Brain Research*, vol. 277, No. 2 (1983), pp. 329-337.

Esch et al., "Isolation and Characterization of the Bovine Hypothalamic Corticotropin-Releasing Factor", *Biochem. & Biophy. Res. Comm.*, vol. 122, No. 3 (1984), pp. 899-905.

Ling et al., "Isolation and Characterization of Caprine Corticotropin-Releasing Factor", *Biochem. & Biophy. Res. Comm.*, vol. 122, No. 3 (1984), pp. 1218-1244.

Melchiorri et al., "Action of Sauvagine on the Mesenteric Vascular Bed of the Dog", *Regulatory Peptides*, vol. 2, (1981), pp. 1-13.

Patthy et al., "Isolation and Amino Acid Sequence of Corticotropin-Releasing Factor from Pig Hypothalami", *Proc. Natl. Acad. Sci. USA*, vol. 82, No. 24, (1985), pp. 8762-8766.

Pinckard et al., "Platelet-Activating Factors", *Inflammation: Basic Principles and Clinical Correlates*, Gallin et al., eds., New York: Raven Press (1988), pp. 139-167.

Stern et al., "Ibuprofen in the Treatment of UV-B-Induced Inflammation," *Arch. Dermatol.*, vol. 121, No. 4, (1985), pp. 508-512.

*Primary Examiner*—Lester L. Lee
*Attorney, Agent, or Firm*—Majestic, Parsons, Siebert & Hsue

[57] ABSTRACT

Administration of a Corticotropin-Releasing Factor (or a salt or analog thereof) decreases the leakage of blood components into brain tissue produced by various adverse medical conditions and reduces bleeding when muscle tissues are cut and handled, such as in plastic and reconstructive surgery. A method of treating a patient for injury to or disease of the brain, central nervous system, or musculature in which edema is a factor comprises administering to the patient a Corticotropin-Releasing Factor (or a salt or analog) in an amount effective to decrease vascular permeability in the injured or diseased brain, nervous system tissue or musculature, and thereby to reduce edema. Administration in accordance with the method can be about two hours before surgery, or can be up to three days after injury.

1 Claim, 1 Drawing Sheet

CONTROL   INVENTIVE TREATMENT

CONTROL   INVENTIVE TREATMENT

METHOD FOR TREATING ENDOTOXIN SHOCK WITH CRF

This invention was made with Government support under Grant No. DA-00091 awarded by the National Institutes of Health. The Government has certain rights in this invention.

This is a division of application Ser. No. 386,885, filed Jul. 28, 1989 and now U.S. Pat. No. 5,137,871.

FIELD OF THE INVENTION

This invention generally relates to a method of reducing edema in connection with brain and musculature injuries, and more particularly to the use of Corticotropin-Releasing Factor or its analogs in reducing edema of the brain and musculature following injury to or disease of these vascular beds.

BACKGROUND OF THE INVENTION

Inflammation is signaled by redness, swelling, heat and pain as a reaction of the body against injury or assault. A variety of chemicals have been implicated as chemical mediators of the inflammatory reaction, including histamine, serotonin, kinins, prostaglandins, platelet-activating factors, leukotrienes, and, from nerve endings, substance P. Mediators of the acute inflammatory reaction seem to play roles in one or more of increasing vascular permeability, attracting leukocytes, producing pain, local edema and necrosis.

A variety of physiologic responses occur from the biological events that constitute the inflammatory processes. For example, Pinckard et al. at Chapter 10 describe platelet-activating factors ("PAF") in the text *Inflammation: Basic Principles and Clinical Correlates* (Gallin et al. Ed. 1988). This family of structurally related compounds appear to promote a variety of physiologic actions that are directly or indirectly related to inflammatory reactions. The authors note that PAF has been implicated in the pathogenesis of human disease conditions such as endotoxin shock and organ transplantation rejection.

There are steroid and non-steroid, anti-inflammatory drugs known to the art. U.S. Pat. No. 4,579,844, inventors Rovee et al., issued Apr. 1, 1986, discloses topically treating an inflammatory condition of the skin by use of the prostaglandin synthetase inhibitor concurrently with a corticosteroid. U.S. Pat. No. 4,404,198, inventor Kelley, issued Sep. 13, 1983, discloses the topical application of a composition including phenyl salicylate to treat inflammation. U.S. Pat. No. 3,980,778, inventors Ayer et al., issued Sep. 14, 1976, discloses a steroid for use in the topical, oral or parenteral treatment of skin and mucous membrane inflammations. Ibuprofen (a known anti-inflammatory agent) has been tested in connection with UV-B-induced inflammation, but was found to have limited usefulness in treating sunburn reaction and is only somewhat more effective than placebo for the relief of symptoms associated with UV-B-induced inflammation after high dose UV-B phototherapy for psoriasis. Stern et al., *Arch. Derm.*, 121, pp. 508–512 (1985).

U.S. Pat. No. 4,801,612, inventor Wei, issued Jan. 31, 1989, discloses the use of inhibiting an inflammatory response in the skin or mucosal membranes of a patient by administering Corticotropin-Releasing Factor, or its analogs.

However, the microcirculation for mammals has its own selective pharmacology for each particular vascular bed. This means that an anti-inflammatory agent useful in one vascular bed, such as the skin and mucosal membranes, cannot predictably be useful with other vascular beds, such as the brain or musculature. For example, histamine, bradykinin, serotonin, or arachidonic acid failed to increase permeability in blood vessels of the pia mater (the innermost vascularized covering of the brain), although these substances are potent edema producing agents in the skin and mucosa. Another example of selective pharmacology is epinephrine, since this endogenous substance constricts blood vessels in the skin but dilates blood vessels in skeletal muscle. Thus, the permeability characteristics of the blood vessels (particularly the post-capillary venules) in a vascular bed such as the brain are not equivalent to those in the skin and mucosa.

Corticotropin-Releasing Factor (hereinafter "CRF") is a 41 amino acid neuropeptide that is present in brain and the peripheral nerve endings, and stimulates ACTH release from pituitary cells. U.S. Pat. No. 4,489,163, inventors Rivier et al., issued Dec. 18, 1984, discloses rat CRF and its analogs. Human CRF has the same sequence as rat CRF. The amino acid sequence of both human and rat CRF is illustrated below:

Ser—Glu—Glu—Pro—Pro—Ile—Ser—Leu—Asp—Leu—Thr—
Phe—His—Leu—Leu—Arg—Glu—Val—Leu—Glu—Met—
Ala—Arg—Ala—Glu—Gln—Leu—Ala—Gln—Gln—Ala—His—
Ser—Asn—Arg—Lys—Leu—Met—Glu—Ile—Ile—NH$_2$

There are a number of analogs of CRF known to the art. U.S. Pat. No. 4,415,558, inventors Vale, Jr. et al., issued Nov. 15, 1983, discloses the synthesis of sheep CRF, analogs, and isolation of the oCRF from ovine hypothalamic extracts. The synthetic oCRF was found to lower blood pressure. The amino acid sequence of ovine (sheep) CRF is illustrated below:

Ser—Gln—Glu—Pro—Pro—Ile—Ser—Leu—Asp—Leu—
Thr—Phe—His—Leu—Leu—Arg—Glu—Val—Leu—Glu—
Met—Thr—Lys—Ala—Asp—Gln—Leu—Ala—Gln—
Gln—Ala—His—Ser—Asn—Arg—Lys—Leu—Leu—Asp—
Ile—Ala—NH$_2$

A generally similar peptide, sauvagine, was described in Regulatory Peptides 2, 1–13 (1981). Sauvagine is a 40 amino acid peptide and has been reported to have biological activity in lowering blood pressure in mammals and stimulating the secretion of ACTH and -endorphin. The amino acid sequence of sauvagine is illustrated below:

pGlu—Gly—Pro—Pro—Ile—Ser—Ile—Asp—Leu—Ser—
Leu—Glu—Leu—Leu—Arg—Lys—Met—Ile—Glu—Ile—
Glu—Lys—Gln—Glu—Lys—Glu—Lys—Gln—Gln—Ala—
Ala—Asn—Asn—Arg—Leu—Leu—Leu—Asp—Thr—
Ile—NH$_2$

U.S. Pat. No. 4,528,189, inventors Lederis et al., issued Jul. 9, 1985, and U.S. Pat. No. 4,533,654, inventors Lederis et al., issued Aug. 6, 1985, disclose peptides similar to the rat and sheep CRF and analogs thereof, and found this white sucker and carp urotensin respectively to stimulate ACTH and to lower blood pressure. The amino acid sequence of carp urotensin is illustrated below:

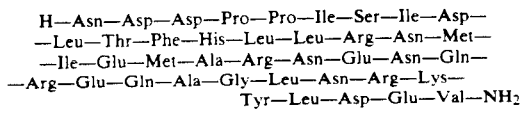

The other CRF-related peptide, white sucker urotensin, has an amino acid sequence the same as the carp urotensin, except the amino acid at the 24 position is Isoleucine and the amino acid at the 27 position is Glutamic Acid.

Ling et al., *BBRC*, Vol. 122, pp. 1218-1224 (1984), disclose the structure of goat CRF, which is the same as that for sheep CRF. Esch et al., *BBRC*, Vol. 122, pp. 899-905 (1984), disclose the structure of bovine CRF which differs from sheep and goat CRF only by one amino acid residue (number 33 which is Asparagine rather than the number 33 Serine of goat and sheep CRF). Porcine CRF has been isolated and characterized by Patthy et al., *Proc. Natl. Acad. Sci.*, Vol. 82, pp. 8762-8766 (1985). Porcine CRF shares a common amino acid sequence (residues 1-39) with rat/human CRF and differs from these only in position 40 and 41. Residue 40 can be either asparagine or isoleucine and residue 41 is phenylalanine-amide.

SUMMARY OF THE INVENTION

It is an object of the present invention to decrease the leakage of blood components into the brain tissue, a condition called vasogenic edema of the brain, that is produced by various adverse medical conditions, such as brain ischemia, brain infarction, intracranial hemorrhage from neurosurgical operations, brain infections and abscesses, brain tumors and traumatic head injuries.

It is another object of the present invention to reduce bleeding when muscle tissues are cut and handled, such as in plastic and reconstructive surgery, abdominal surgery, back operations, orthopedic surgery or other traumatic lacerations (for example, cuts from broken glass or knife wounds).

It is yet another object of the present invention to decrease the leakage of blood components in conjunction with spinal cord injuries.

In one aspect of the present invention, a method of treating a patient for injury to or disease of the brain, central nervous system, or musculature in which edema is a factor comprises administering to the patient a Corticotropin-Releasing Factor (or a salt or analog thereof) in an amount effective to decrease vascular permeability in the injured or diseased brain, nervous system tissue, or musculature, and thereby to reduce edema.

Brain edema refers to a condition in which there is increased water content in brain tissues. This condition occurs when there is a breakdown in the function of blood vessels that normally separate blood constituents from brain tissues. Brain blood vessels become more permeable when they are injured by a lack of oxygen, by toxic substances generated in injured tissues, or by unknown causes such as those associated with brain hemorrhage of the newborn. The medical conditions associated with brain edema are: brain ischemia, brain infarction, brain tumors, brain infections and abscesses, brain trauma and contusions, and secondary brain damage arising from neurosurgical operations. Spinal cord injuries pose similar problems to brain damage, and the spinal cord is, like brain cells, nervous tissue.

Administration in accordance with the invention reduces the permeability of brain and central nervous system blood vessels and is of therapeutic value in the treatment of brain and central nervous system injuries. Thus, for example, the serious medical emergency posed by brain edema, where the increased amounts of water compress and distort tissue architecture and impede delivery of oxygen to brain cells, can be substantially avoided or alleviated. Administrations in accordance with the invention also provide clinical benefits when used to limit or minimize leakage of blood constituents into tissue during surgery.

DETAILED DESCRIPTION OF THE PREFERRED EMBODIMENTS

Figure 1:
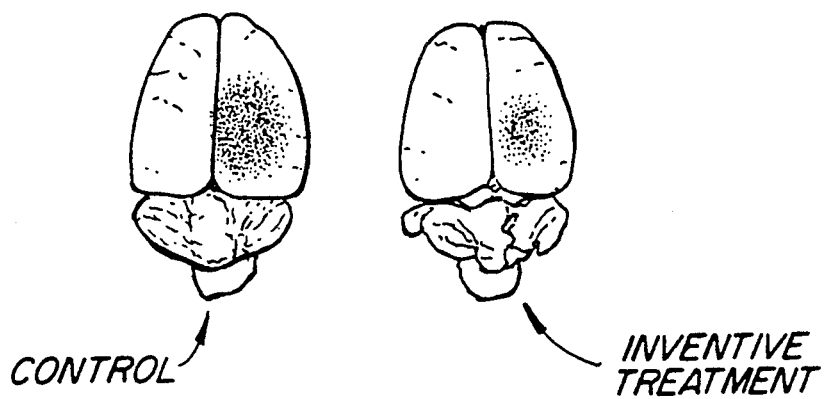
FIG. 1 shows two rat brains one hour after injury. The cortex stained with a blue dye (shown by shading) delineates the area of increased vascular permeability produced by cold injury. On the left is the brain of a rat treated with saline. On the right is the brain of a rat treated in accordance with the invention; and, FIG. 2 shows two rat muscle tissue sections taken ½ hour after muscle injury (a 4 cm mid-line incision, or celiotomy). The tissue stained with a blue dye (shown by shading) delineates the area of increased vascular permeability due to the surgical injury. On the left is the tissue of a rat treated with saline. On the right is the tissue of a rat treated in accordance with the invention.

When an injury to the brain occurs, such as brain ischemia, or infarction, vasogenic edema occurs and the increased amounts of water compress and distort brain tissue architecture and impede the delivery of oxygen to brain cells. The patient can lose consciousness and stop breathing. I have discovered that Corticotropin-Releasing Factor ("CRF"), its analogs, and related peptides (e.g., sauvagine and urotensin I) are effective in reducing the leakiness in the blood vessels of the brain (technically quantified as a change in vascular permeability) after injury. This discovery was surprising because the blood vessels of the brain, in contrast to the vessels found in the skin and mucosa, have "tighter" junctions, and normally do not respond to the inflammatory mediators that promote leakage of blood vessels in the skin.

By "CRF" is meant herein mammalian Corticotropin-Releasing Factor, including that isolatable from rat, human, beef, goat, pig or sheep. Analogs of CRF include sauvagine, carp urotensin and sucker urotensin (all of which have been isolated from lower vertebrates), and those synthetic peptide structures analogous to CRF and disclosed in U.S. Pat. Nos. 4,415,558, 4,489,163, 4,553,654, and 4,528,189, incorporated herein by reference.

The effective neuropeptides for use in the present invention may be isolated from the above-noted natural sources or may be readily prepared synthetically, such as by solid phase peptide synthesis techniques. For example, the synthesis can be commenced from the carboxyl terminal end of the peptide by coupling the appropriate amino acid, e.g. L-Arginine, L-Isoleucine, L-Phenylalanine or L-Valine, to a suitable resin support, such as a p-methyl benzhydrylamine resin, a chloromethylated resin or a hydroxymethyl resin.

The coupling reaction may be carried out with the aid of a carboxyl group activating compound, such as Dicyclohexylcarbodiimide, and with the α-amino group of the amino acid protected with a protecting group, such as t-butyloxycarbonyl (BOC), benzyl(BZL), p-methylbenzyl (MBZL), t-amyloxycarbonyl(AOC), tosyl(TOS), o-bromobenzyloxycarbonyl(BrZ), cyclohexyl (OHEX), or dichlorobenzyl(BZLCl$_2$). Following this coupling reaction, the α-amino protecting group is removed, such as by using trifluoroacetic acid in methylene chloride, trifluoroacetic alone or HCl in dioxane, with the deprotection being carried out at a temperature between about 0° C. and room temperature. Thereafter, each succeeding amino acid in the sequence is coupled in the same manner stepwise in the desired order, culminating in the addition of the final amino acid (e.g., L-Serine, L-Asparagine or L-Glutamine) to obtain the desired peptide.

As an alternative to adding each amino acid separately to the reaction, some may be coupled prior to addition to the solid phase reactor. Each protected amino acid or amino acid sequence is introduced into the solid phase reactor in excess (about a three- or fourfold excess), and the coupling may be carried in a medium of dimethylformamide:methylene chloride 1:1, or in dimethylformamide or methylene chloride alone. The success of the coupling reaction at each stage of the synthesis may be monitored by the ninhydrin reaction.

After the final amino acid in the sequence has been coupled, the deprotection step is carried out by treatment with a reagent such as hydrogen fluoride.

When a p-methyl benzhydryl amine resin has been used as the resin support, the peptide cleaved (by treatment with a reagent such as hydrogen fluoride) from the resin will be in the carboxyl terminal amide form. When a chloromethylated resin or a hydroxymethyl resin has been used as the resin support, the peptide cleaved from the resin support will be in the form of the carboxyl terminal benzyl ester, which may then be readily converted by methods well known in the art to provide the carboxyl terminal amide form of the peptide.

Therapeutically effective doses of CRF or its analogs in practicing this invention are at least about 0.1 μg/kg, more preferably from about 1 to about 200 μg/kg, and most preferably are from about 5 to about 100 μg/kg. A particularly preferred dose is about 30 μg/kg administered i.v. The dose may be infused slowly intradermally or subcutaneously, or may be injected directly into an afflicted body part. When injected locally, doses of about 10 to about 100 μg per local administration (i.e. about 0.1 to about 1 μg/kg body weight) are preferred.

The neuropeptides should be administered under the guidance of a physician. Administration is preferably by intravenous, intradermal or subcutaneous injection. Administration can be about two hours before deliberate lacerations of the musculature, brain surgery, or the like, and can be up to three days after surgery or accidental injury. The drug is preferably delivered via the bloodstream, but local injections into the cerebrospinal fluid, brain, or into the muscle can be used for administration.

The active neuropeptide may be administered in combination with a pharmaceutically acceptable carrier, such as isotonic saline, phosphate buffer solution, or the like. Topical administration is not preferred, since CRF or an analog is a large molecule (e.g., 40 or 41 amino acids) and is not as efficiently delivered to the site of action as when administered by injection.

Although the peptides are generally water soluble as typically synthesized, they may be administered in the form of pharmaceutically acceptable non-toxic salts, such as acid addition salts. Illustrative acid addition salts are hydrochloride, hydrobromide, sulfate, sulphate, acetate, citrate, benzoate, succinate, malate, ascorbate, tartrate, or the like.

An in vivo model of injury to study brain edema has been developed as a reproducible edema model, which has the features of immediate cortical damage followed by the subsequent development of brain edema. This model is described by Chan et al., *Brain Research* 277, pp. 329–337 (1983). The model uses rats which are anesthetized. A 2.5 cm incision is made over the sagittal suture and the bone of the right hemisphere exposed. A 60 mm$^2$ plate attached to a brass cup filled with dry ice-acetone mixture, with a temperature of −50° C., is applied to the rat skull for one minute. The animals are sacrificed at various intervals after the onset of cold-injury. A dye is administered intravenously before the freezing. Cortical slices are then obtained of the brain.

EXAMPLE I 16 male rats were randomly divided into eight pairs and one rat in each pair received either saline or CRF (subcutaneously twice at 30 μg/kg, 30 min and 10 min before cold injury). The animals were anesthetized with sodium pentobarbital, 60 mg/kg intraperitoneally, and injected with Monastral blue, 60 mg/kg intravenously. A cold probe was applied onto the skull for 4 min and the brains taken out 1 hour after cold injury. The staining of brain tissues with Monastral blue, a colloidal pigment that gets trapped between the albuminal surface of the endothelial cell and the basement membrane, was proportional to the degree of vascular leakage. The results from the first pair are shown as FIG. 1. Table I summarizes the data.

TABLE I

| Treatment | CRF and Freeze Injury to Brain | | |
|---|---|---|---|
| | Area mm$^2$ | Intensity | Lesion Size |
| Saline | 43.4 ± 1.7 | 2.2 ± 0.04 | 96 ± 4 |
| CRF | 20.8 ± 1.2 | 2.0 ± 0.05 | 43 ± 3 |

The size of the lesion, measured as area in mm$^2$, and the degree of staining intensity, were quantified using an image-analysis software program called JAVA (Jandel Corporation, San Rafeal, Calif.). The stain intensity, given in arbitrary units, was internally calibrated using Monastral blue solutions (1–30 mg/ml) placed on white filter paper. Values are mean ±S. E. M.

As can be seen visually from the shading of FIG. 1, the area and intensity of vascular permeability produced by cold injury was greatly less for the brain of a rat treated in accordance with the invention by administration of CRF than the brain of a rat treated with saline. As can be seen by the data of Table I, the lesion size of the CRF-treated group was only 44% that of the saline-treated group.

An observer, unaware of the rat's pretreatment and asked to distinguish between more damaged brains from the less damaged brain, is able to correctly guess 8 out of 8 times the assignment of the brains to either the saline or CRF group. Thus, the ability of CRF to suppress vascular leakage in the brain is shown.

EXAMPLE II

In a second set of experiments, the brain surface, namely the cerebral cortex, was injured by freezing and the water and sodium content were measured in the cerebral cortex and in the basal ganglia, a part of the brain away from the freeze zone. The water and sodium content of the brain tissue served as an index of brain edema. After freeze injury, the water and sodium content of the cerebral cortex were evaluated relative to non-frozen tissues. CRF administered in two separate doses of 30 μg/kg subcutaneously, one dose 15 min. before the injury and the second dose 90 min. after the first dose, inhibited the two indices of brain edema. Table II summarizes the data.

TABLE II

| TREATMENT | WATER CONTENT % | SODIUM mEg/kg dry wt |
|---|---|---|
| CEREBRAL CORTEX | | |
| Saline | 87 ± 0.2 | 310 ± 9 |
| CRF | 77 ± 4* | 271 ± 8* |
| BASAL GANGLIA | | |
| Saline | 75 ± 1 | 213 ± 4 |
| CRF | 76 ± 1 | 215 ± 9 |

Values are ± S.E.M., N = 5 animals per group
*P < .05 vs Saline Controls
Male Sprague-Dawley rats. 300-325 g. anesthetized with ketamine-acepromazine, were injected saline or CRF (30 μg/kg s.c. 2×) and injury to cerebral cortex was produced by applying a cold probe to the skull for 1 min. Brain tissues were obtained 3 hr later and analyzed for water and sodium content.

As can be seen from the data of Table II, the saline treated rats had increased water content at the cerebral cortex injury and substantially increased sodium with respect to the rats treated in accordance with the invention with CRF. That is, since the water and sodium content of the brain tissue served as an index of brain edema, the CRF treated rats were shown to have a suppressed vascular leakage due to cerebral cortex injury; however, the inventive treatment did not affect the water or sodium content in the non-injured basal ganglia.

EXAMPLE III

Figure 2:
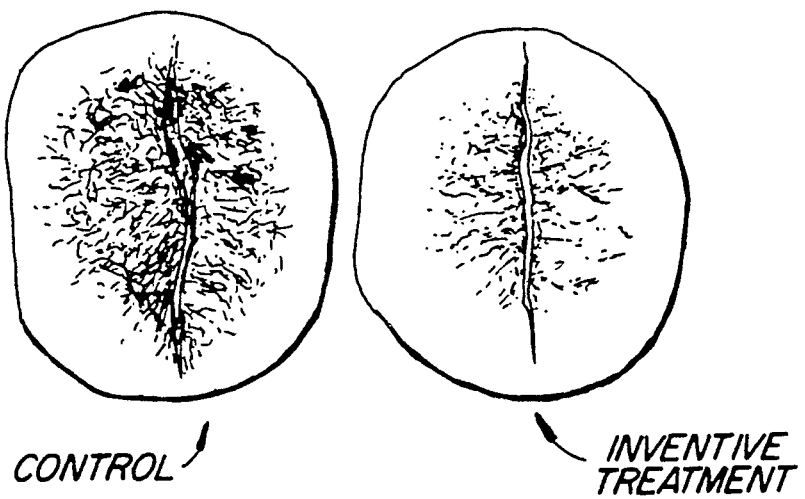

Experiments were conducted on male Sprague-Dawley rats 243±15 gm (S. D., Simonsen Labs., Gilroy, Calif.) anesthetized with sodium pentobarbital, 60 mg/kg i.p. Monastral blue, 60 mg/kg i.v., was injected 0.2 ml/100 g. 3 min. before a 4 cm midline incision through the abdominal muscle wall (celiotomy). Saline or CRF was administered to randomizd pairs with N=8 rats per group. The size of the lesion, measured as area in mm², an its light intensity, were quantified using the JAVA image-analysis software program. The light intensity, given in arbitrary units, was internally calibrated using Monastral blue solutions (1-30 mg/ml) placed on white filter paper. Values are mean ±S. E. M. FIG. 2 illustrates the respective amount of vascular permeability for one pair of rats (control and treated). Tables III and IV set out data from these experiments.

TABLE III

Dose-Response Data for CRF
and Vascular Leakage After Celiotomy
CRF: injected at various doses subcutaneously 30 min
before a 4 cm midline incision, tissues taken 0.5 hr
after surgery.

| Treatment | Area mm² | Intensity | Lesion Size |
|---|---|---|---|
| Saline | 778 ± 34 | 2.1 ± 0.03 | 1624 ± 57 |
| CRF 15 μg/kg | 505 ± 16 | 2.0 ± 0.03 | 1031 ± 44 |
| CRF 30 μg/kg | 361 ± 18 | 1.9 ± 0.05 | 676 ± 47 |
| CRF 60 μg/kg | 257 ± 3 | 1.8 ± 0.05 | 468 ± 19 |

TABLE IV

Long Duration of CRF Before Surgery
CRF: 30 μg/kg s.c. injected 2 hr before a 4 cm midline
incision, tissues taken 0.5 hr after surgery

| Treatment | Area mm² | Intensity | Lesion Size |
|---|---|---|---|
| Saline | 735 ± 32 | 2.1 ± 0.02 | 1547 ± 62 |
| CRF | 477 ± 31 | 1.9 ± 0.03 | 919 ± 51 |

The celiotomy data illustrate the efficacious results from use of CRF in accordance with the invention as a result of musculature injury. Thus, the data of Table III show that vascular leakage was reduced in a dose dependent manner since the lesion size of the CRF-treated groups were 63%, 42% and 29% that of the saline-treated group, respectively.

Table IV shows that CRF can be administered even two hours before musculature injury and still significantly reduce vascular leakage, since the lesion size of the CRF-treated group illustrated by Table IV was 59% that of the saline-treated group.

Increased vascular permeability occurs when blood vessels are exposed to toxic substances generated in injured tissues. These substances, called inflammatory mediators, include chemicals such as serotonin, substance P, bradykinin, neurotensin, and histamine. It has previously been shown that CRF will antagonize the edema-producing properties of these mediators when injected into the rat pawskin. These mediators act on blood vessels principally in the skin and mucosa. But there is another, recently discovered, important class of inflammatory mediators called platelet-activating factors (PAF), which act not only on blood vessels in the skin and mucosa, but also on small blood vessels in the lung and other visceral organs.

PAF-acether is a prototype member of the PAF family. On a molar basis, PAF-acether is two to four orders of magnitude more potent than any other currently known vasoactive substance. PAF are rapidly synthesized by inflammatory cells when responding to injury and increase blood vessel permeability. PAF have been shown to be causally related to a variety of adverse medical conditions and may account for the pathologic and symptomatic processes of the disease state. For example, when bacteria are present in the bloodstream and produce endotoxins, the endotoxins stimulate the release of PAF and other factors which then increase vascular permeability throughout various organs of the body, but especially the lung, and produce the condition known as endotoxin (or septic) shock which is manifested as a fall in blood pressure, blood volume, and hemoconcentration.

Another condition in which PAF have been implicated is in the deterioration of organs after they have been removed from the body. This deterioration is a natural consequence of increased water permeation of healthy tissues. Thus, an agent capable of antagonizing PAF actions will have therapeutic benefit in endotoxin shock and in the preservation of organs, such as for transplant of kidneys, heart, liver, and lungs, and for amputated limbs or digits prior to re-attachment to the body. In such uses the vasculature of the organs to be transplanted are preferably perfused with a solution containing about 5 to about 500 μg of CRF or CRF analogs.

The data of Table V shows that the increased vascular permeability produced by PAF-acether is antagonized by CRF.

TABLE V

CRF Inhibits Vascular Leakage Produced by PAF-Acether
CRF: 30 μg/kg s.c. injected 30 min before subcutaneous
injection of PAF-acether (1 μg/0.1 ml/rat) into the
abdomen; muscle removed 0.5 hr later.

| Treatment | Area mm$^2$ | Intensity | Lesion Size |
|---|---|---|---|
| Saline | 327 ± 22 | 1.8 ± 0.04 | 589 ± 43 |
| CRF | 188 ± 16 | 1.4 ± 0.05 | 260 ± 26 |

The muscle lesion size of the CRF-treated group was 44% that of the saline-treated control group, illustrating the beneficial use of the invention in conditions such as where patients are experiencing endotoxin shock due to PAF.

It is to be understood that while the invention has been described above in conjunction with preferred specific embodiments, the description and examples are intended to illustrate and not limit the scope of the invention, which is defined by the scope of the appended claims.

It is claimed:

1. A method of treating endotoxin shock in a patient comprising:

administering to the patient a corticotropin-releasing factor, including salts and analogs thereof, in an amount effective to antagonize inflammatory mediators.